United States Patent
Ono et al.

(10) Patent No.: US 9,673,048 B2
(45) Date of Patent: Jun. 6, 2017

(54) METHOD OF PRODUCING THIN FILM TRANSISTOR, THIN FILM TRANSISTOR, DISPLAY DEVICE, IMAGE SENSOR, AND X-RAY SENSOR

(71) Applicant: FUJIFILM CORPORATION, Minato-ku, Tokyo (JP)

(72) Inventors: Masashi Ono, Kanagawa (JP); Masahiro Takata, Kanagawa (JP); Toshiya Ideue, Kanagawa (JP); Atsushi Tanaka, Kanagawa (JP); Masayuki Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 178 days.

(21) Appl. No.: 14/571,293

(22) Filed: Dec. 16, 2014

(65) Prior Publication Data
US 2015/0103977 A1 Apr. 16, 2015

Related U.S. Application Data

(63) Continuation of application No. PCT/JP2013/065489, filed on Jun. 4, 2013.

(30) Foreign Application Priority Data

Jun. 20, 2012 (JP) ................................. 2012-139187

(51) Int. Cl.
*H01L 27/12* (2006.01)
*H01L 29/66* (2006.01)
(Continued)

(52) U.S. Cl.
CPC ....... *H01L 21/02628* (2013.01); *G01N 23/04* (2013.01); *G01T 1/24* (2013.01);
(Continued)

(58) Field of Classification Search
CPC ........... H01L 27/1225; H01L 29/78693; H01L 27/1292; H01L 29/263; H01L 29/267; H01L 29/6869; H01L 29/78696
See application file for complete search history.

(56) References Cited

U.S. PATENT DOCUMENTS

| | | | | |
|---|---|---|---|---|
| 7,674,662 B2* | 3/2010 | Ye | ........................ | H01L 29/7869 438/151 |
| 8,012,794 B2* | 9/2011 | Ye | ..................... | H01L 21/02521 257/43 |

(Continued)

FOREIGN PATENT DOCUMENTS

| | | |
|---|---|---|
| JP | 2010-018479 A | 1/2010 |
| JP | 2010-021333 A | 1/2010 |

(Continued)

OTHER PUBLICATIONS

Machine Translation of JP2010-074061, Fujifilm Corp., Apr. 2010, 24 pages.*

(Continued)

*Primary Examiner* — Evan Pert
(74) *Attorney, Agent, or Firm* — SOLARIS Intellectual Property Group, PLLC

(57) ABSTRACT

A method of producing a thin film transistor includes: forming a gate electrode; forming a gate insulating film that contacts the gate electrode; forming, by a liquid phase method, an oxide semiconductor layer arranged facing the gate electrode with the gate insulating film provided therebetween, the oxide semiconductor layer including a first region and a second region, the first region being represented by $In_{(a)}Ga_{(b)}Zn_{(c)}O_{(d)}$, the second region being represented by $In_{(e)}Ga_{(f)}Zn_{(g)}O_{(h)}$, and the second region being located farther from the gate electrode than the first region; and forming a source electrode and a drain electrode that are (Continued)

arranged apart from each other and are capable of being conductively connected through the oxide semiconductor layer.

18 Claims, 9 Drawing Sheets

(51) Int. Cl.
  *H01L 31/032* (2006.01)
  *H01L 21/02* (2006.01)
  *H01L 29/26* (2006.01)
  *H01L 29/786* (2006.01)
  *H01L 27/146* (2006.01)
  *G01N 23/04* (2006.01)
  *G01T 1/24* (2006.01)

(52) U.S. Cl.
  CPC .. *H01L 21/02381* (2013.01); *H01L 21/02422* (2013.01); *H01L 21/02472* (2013.01); *H01L 21/02483* (2013.01); *H01L 21/02488* (2013.01); *H01L 21/02554* (2013.01); *H01L 21/02565* (2013.01); *H01L 21/02592* (2013.01); *H01L 27/1225* (2013.01); *H01L 27/1292* (2013.01); *H01L 27/14632* (2013.01); *H01L 27/14676* (2013.01); *H01L 29/263* (2013.01); *H01L 29/66969* (2013.01); *H01L 29/7869* (2013.01); *H01L 29/78693* (2013.01); *H01L 29/78696* (2013.01); *H01L 31/032* (2013.01)

(56) References Cited

U.S. PATENT DOCUMENTS

| | | | | |
|---|---|---|---|---|
| 8,188,480 B2* | 5/2012 | Itai | .................... | H01L 29/78618 257/288 |
| 8,367,486 B2* | 2/2013 | Sakata | ................ | H01L 29/7869 257/E21.134 |
| 8,742,414 B2* | 6/2014 | Kim | .................. | H01L 21/02554 252/521.6 |
| 9,202,926 B2* | 12/2015 | Kishi | .................. | H01L 29/7869 |
| 9,318,507 B2* | 4/2016 | Miki | ................... | H01L 27/1225 |
| 2005/0275038 A1* | 12/2005 | Shih | .................. | H01L 29/78633 257/382 |
| 2008/0258140 A1* | 10/2008 | Lee | .................... | H01L 21/02554 257/43 |
| 2008/0315200 A1* | 12/2008 | Kim | .................... | H01L 29/7869 257/57 |
| 2010/0001274 A1* | 1/2010 | Ye | ..................... | H01L 21/02521 257/57 |
| 2010/0163863 A1* | 7/2010 | Yaegashi | ............ | H01L 29/7869 257/43 |
| 2010/0320458 A1* | 12/2010 | Umeda | ................ | C01G 15/006 257/43 |
| 2010/0320459 A1* | 12/2010 | Umeda | ............. | H01L 21/02554 257/43 |
| 2011/0140100 A1* | 6/2011 | Takata | ................ | H01L 29/7869 257/43 |
| 2011/0220895 A1* | 9/2011 | Hirai | ................... | H01L 29/7869 257/57 |
| 2012/0056173 A1* | 3/2012 | Pieralisi | ............ | H01L 23/53238 257/43 |
| 2012/0061661 A1* | 3/2012 | Liu | .................... | H01L 29/78606 257/43 |
| 2013/0251943 A1* | 9/2013 | Pei | ........................... | H01B 1/02 428/141 |
| 2013/0280859 A1* | 10/2013 | Kim | .................... | H01L 29/7869 438/104 |
| 2014/0103341 A1* | 4/2014 | Umeda | ............. | H01L 29/78693 257/43 |
| 2014/0231798 A1* | 8/2014 | Ono | .................... | H01L 29/7869 257/43 |
| 2014/0367674 A1* | 12/2014 | Shimoda | .................. | H01B 1/08 257/43 |
| 2015/0087110 A1* | 3/2015 | Facchetti | .......... | H01L 21/02381 438/104 |
| 2015/0103977 A1* | 4/2015 | Ono | .................. | H01L 27/14632 378/62 |
| 2016/0005879 A1* | 1/2016 | Takata | .............. | H01L 29/66969 257/43 |
| 2016/0042947 A1* | 2/2016 | Nakamura | ........ | H01L 29/66969 257/43 |
| 2016/0225859 A1* | 8/2016 | Takata | .................... | H01L 29/24 |
| 2016/0276492 A1* | 9/2016 | Takeda | .............. | H01L 21/02472 |

FOREIGN PATENT DOCUMENTS

| | | |
|---|---|---|
| JP | 2010-021555 A | 1/2010 |
| JP | 2010-074061 A | 4/2010 |
| JP | 2010-263103 A | 11/2010 |
| JP | 2012-059860 A | 3/2012 |
| TW | 201222823 A | 6/2012 |

OTHER PUBLICATIONS

Machine Translation of JP 2010-021333, Fujifilm Corp., Jan. 2010, 28 pages.*
Machine Translation of JP 2010-263103, Konica Minolta Holdings Inc., Nov. 2010, 31 pages.*
Korean Office Action dated Dec. 9, 2015, issued in corresponding Korean Patent Application.
Japanese Office Action dated Mar. 10, 2015, issued in corresponding Japanese Patent Application.
Written Opinion of the ISA issued in International Application No. PCT/JP2013/065489 on Jul. 9, 2013.
International Search Report issued in International Application No. PCT/JP2013/065489 on Jul. 9, 2013.
English language translation of the following: Office action dated Dec. 14, 2016 from the TIPO in a Taiwan patent application related to the instant patent application.

* cited by examiner

METHOD OF PRODUCING THIN FILM TRANSISTOR, THIN FILM TRANSISTOR, DISPLAY DEVICE, IMAGE SENSOR, AND X-RAY SENSOR

CROSS-REFERENCE TO RELATED APPLICATIONS

This application is a continuation application of International Application No. PCT/JP2013/065489, filed Jun. 4, 2013, the disclosure of which is incorporated herein by reference in its entirety. Further, this application claims priority from Japanese Patent Application No. 2012-139187, filed Jun. 20, 2012, the disclosure of which is incorporated herein by reference in its entirety.

TECHNICAL FIELD

This invention relates to a method of producing a thin film transistor, a thin film transistor, a display device, an image sensor, and an x-ray sensor.

BACKGROUND ART

Transparent amorphous oxide semiconductor (TAOS) materials as typified by materials of In—Ga—Zn—O system (hereinafter, simply referred to as InGaZnO) exhibit higher mobility compared to a-Si, and therefore have been attracting much attention as materials that constitutes an active layer (channel layer) of a thin film transistor (TFT) for driving a large high-definition display. In particular, with regard to an InGaZnO-TFT (TAOS-TFT) deposited by vacuum deposition such as sputtering, technical consideration of issues relating to mass production has been advanced, and the technology has nearly reached a practical level (for example, see Japanese Patent Application Laid-Open (JP-A) No. 2010-21555).

On the other hand, as a technique for fabricating large-area TAOS-TFTs at low cost, research and development of a liquid phase method have been actively carried out (for example, see JP-A Nos. 2010-21333 and 2010-18479).

SUMMARY OF INVENTION

Technical Problem

The liquid phase method requires annealing at a higher temperature to realize high mobility, and it is difficult to realize high mobility by the liquid phase method.

An object of the invention is to provide a method of producing a thin film transistor exhibiting high mobility (≥1 cm$^2$/Vs), in which a transparent amorphous oxide semiconductor layer is formed using a liquid phase method, and annealing is conducted at a relatively low temperature; a thin film transistor produced by the method; and a display device, an image sensor, and an X-ray sensor each provided with the thin film transistor.

Solution to Problem

In order to achieve the above object, the following invention is provided.
<1> A method of producing a thin film transistor, comprising:
  forming a gate electrode;
  forming a gate insulating film that contacts the gate electrode;
  forming, by a liquid phase method, an oxide semiconductor layer arranged facing the gate electrode with the gate insulating film provided therebetween, the oxide semiconductor layer comprising a first region and a second region, the first region being represented by $In_{(a)}Ga_{(b)}Zn_{(c)}O_{(d)}$, wherein a≥0, b≥0, c≥0, a+b+c=1, d>0, b≤1/3, and b≥−10a/7+1 are satisfied, the second region being represented by $In_{(e)}Ga_{(f)}Zn_{(g)}O_{(h)}$, wherein e≥0, f≥0, g≥0, e+f>0, and h>0 are satisfied, and the second region being located farther from the gate electrode than the first region; and
  forming a source electrode and a drain electrode that are arranged apart from each other and are capable of being conductively connected through the oxide semiconductor layer.
<2> The method of producing a thin film transistor according to <1>, wherein, in the forming of the oxide semiconductor layer, a raw material solution comprising a solvent and at least one selected from the group consisting of a metal alkoxide, a β-diketone complex, and a nitrate is used to form the oxide semiconductor layer.
<3> The method of producing a thin film transistor according to <1>, wherein, in the forming of the oxide semiconductor layer, a raw material solution comprising a solvent and at least one selected from the group consisting of a metal alkoxide and a β-diketone complex is used to form the oxide semiconductor layer.
<4> The method of producing a thin film transistor according to <1>, wherein, in the forming of the oxide semiconductor layer, a raw material solution comprising a solvent and a metal alkoxide is used to form the oxide semiconductor layer.
<5> The method of producing a thin film transistor according to <4>, wherein the raw material solution comprises an aminoethanol as the solvent.
<6> The method of producing a thin film transistor according to <1>, wherein, in the forming of the oxide semiconductor layer, a raw material solution comprising a solvent and a β-diketone complex is used to form the oxide semiconductor layer.
<7> The method of producing a thin film transistor according to <6>, wherein the raw material solution comprises a β-diketone as the solvent.
<8> The method of producing a thin film transistor according to any one of <1> to <7>, wherein the first region is in a composition range further satisfying b≤a/2−1/10 and b≥−3a/2+11/10.
<9> The method of producing a thin film transistor according to <8>, wherein the first region is in a composition range further satisfying b≥1/20 and c≥1/20.
<10> The method of producing a thin film transistor according to any one of <1> to <9>, wherein the second region has a composition satisfying f/(e+f)>0.250.
<11> The method of producing a thin film transistor according to any one of <1> to <10>, wherein the second region has a composition satisfying f/(e+f)<0.875.
<12> The method of producing a thin film transistor according to any one of <1> to <11>, wherein a film thickness of the second region is more than 10 nm but less than 70 nm.
<13> The method of producing a thin film transistor according to any one of <1> to <12>, wherein the oxide semiconductor layer is amorphous.
<14> The method of producing a thin film transistor according to any one of <1> to <13>, wherein, in the forming of the oxide semiconductor layer, an oxide precursor film including at least one metal organic compound selected from the group consisting of a metal alkoxide and a β-diketone complex is formed, and the oxide precursor film is subjected to a heat treatment at a temperature equal to or higher than a thermal decomposition temperature of the metal organic compound.

<15> The method of producing a thin film transistor according <14>, wherein the heat treatment is carried out at 400° C. or higher.

<16> A thin film transistor, produced by the method according to any one of <1> to <15>.

<17> A display device, comprising the thin film transistor according to <16>.

<18> An image sensor, comprising the thin film transistor according to <16>.

<19> An X-ray sensor, comprising the thin film transistor according to <16>.

<20> An X-ray digital imaging device, comprising the X-ray sensor according to <19>.

<21> The X-ray digital imaging device according to <20>, capable of capturing a moving image.

Advantageous Effects of Invention

According to the invention, there are provided a method of producing a thin film transistor exhibiting high mobility ($\geq 1$ cm$^2$/Vs), in which a transparent amorphous oxide semiconductor layer is formed using a liquid phase method, and annealing is conducted at a relatively low temperature; a thin film transistor produced by the method; and a display device, an image sensor, and an X-ray sensor each provided with the thin film transistor.

DESCRIPTION OF EMBODIMENTS

Figure 1:
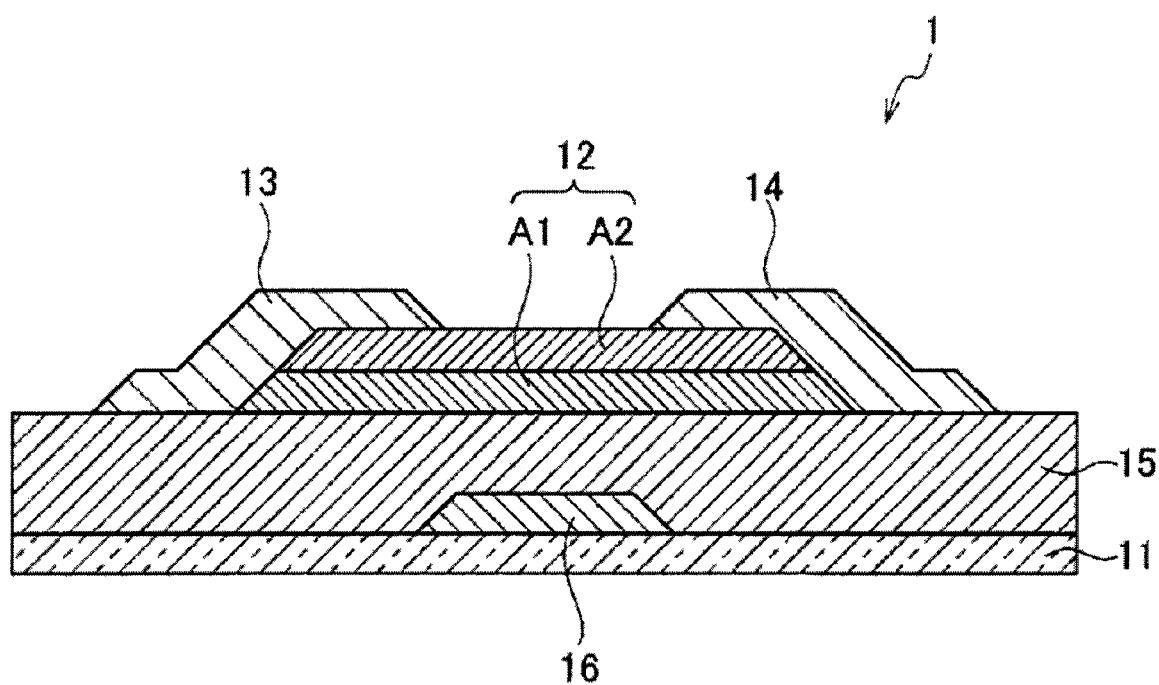
FIG. 1 shows a schematic view of a structure of an example of a thin film transistor (bottom-gate and top-contact type) produced according to the invention.

Hereinbelow, the method of producing a thin film transistor according to the invention, and the display device, sensor, and X-ray sensor (digital imaging device) each provided with a thin film transistor produced according to the invention are described more specifically with reference to the accompanying drawings. In the drawings, members (constituent elements) having the same or corresponding functions are denoted by the same reference numeral, and description is arbitrarily omitted.

As a result of an intensive study regarding a method of producing a thin film transistor having a mobility of 1 cm$^2$/Vs or more by forming an oxide semiconductor layer using a liquid phase method, it was found that a thin film transistor having a mobility of 1 cm$^2$/Vs or more can be produced at a relatively low temperature by forming an oxide semiconductor layer to have a multi-layered structure and controlling the region on the gate electrode side in a specific composition range.

That is, the method of producing a thin film transistor according to the invention includes: a step of forming a gate electrode; a step of forming a gate insulating film that contacts the gate electrode; a step of forming, by a liquid phase method, an oxide semiconductor layer arranged facing the gate electrode with the gate insulating film provided therebetween, the oxide semiconductor layer including a first region and a second region, the first region being represented by In$_{(a)}$Ga$_{(b)}$Zn$_{(c)}$O$_{(d)}$, wherein a$\geq$0, b$\geq$0, c$\geq$0, a+b+c=1, d>0, b$\leq$1/3, and b$\geq$-10a/7+1 are satisfied, the second region being represented by In$_{(e)}$Ga$_{(f)}$Zn$_{(g)}$O$_{(h)}$, wherein e$\geq$0, f$\geq$0, g$\geq$0, e+f>0, and h>0 are satisfied, and the second region being located farther from the gate electrode than the first region; and a step of forming a source electrode and a drain electrode that are arranged apart from each other and are capable of being conductively connected through the oxide semiconductor layer.

Thin Film Transistor

Figure 2:
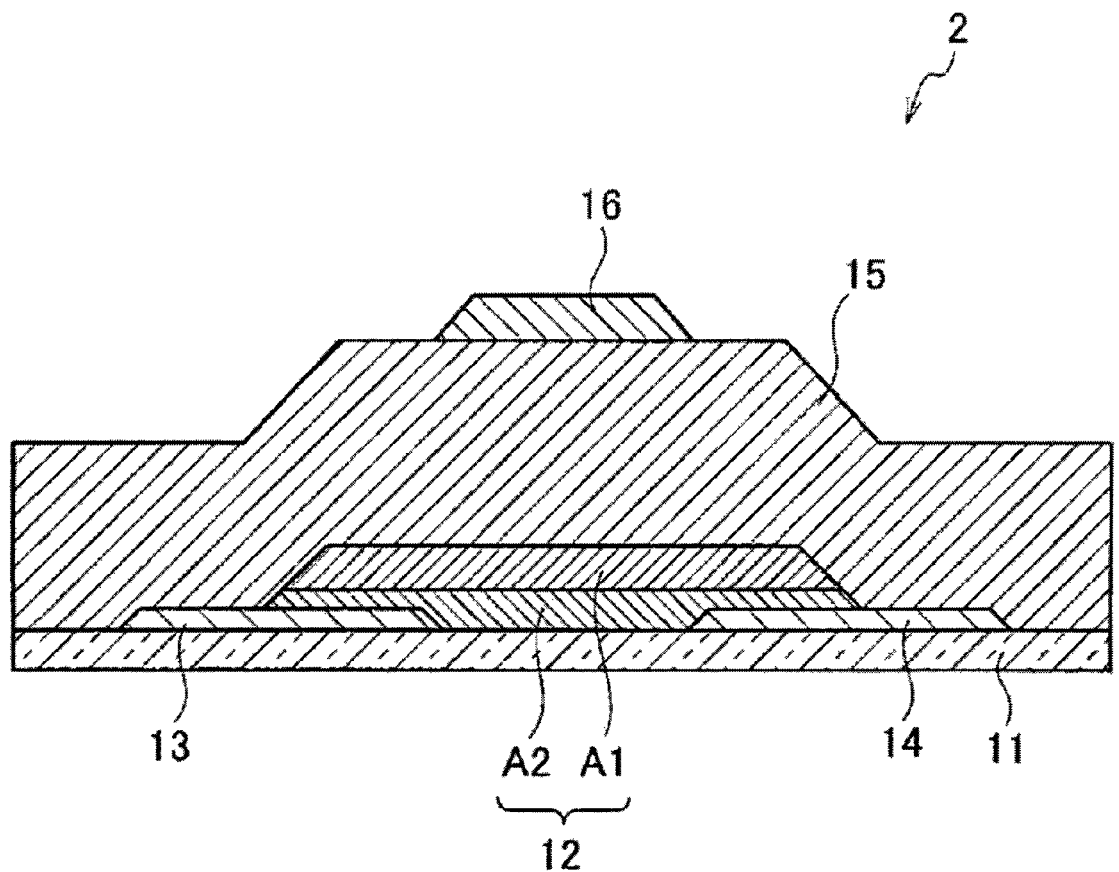
FIG. 2 shows a schematic view of a structure of an example of a thin film transistor (top-gate and bottom-contact type) produced according to the invention.

The configuration of the thin film transistor (sometimes referred to as "TFT") produced by the method of producing a thin film transistor according to the invention is described with reference to the drawings. Here, TFTs shown in FIGS. 1 and 2 are specifically described as representative examples. However, the invention can be applied to the production of TFTs having other forms (configurations).

The device structure of the TFT produced according to the invention may be any of a so-called bottom gate type (also called an inverse stagger structure) and a top-gate type (also called a stagger structure), based on a position of the gate electrode. The top-gate type is a form in which a gate electrode is provided at an upper side of a gate insulating film and an active layer is formed at a lower side of the gate insulating film, when a substrate having a TFT formed thereon is a lowermost layer. The bottom gate type is a form in which a gate electrode is provided at a lower side of a gate insulating film and an active layer is formed at an upper side of the gate insulating film, when a substrate having a TFT formed thereon is a lowermost layer.

The device structure of the TFT produced according to the invention may be any of a so-called top-contact type and a bottom-contact type, based on a contact portion between an oxide semiconductor layer and a source electrode and a drain electrode (sometimes referred to as "source and drain electrodes"). The bottom-contact type is a form in which the source and drain electrodes are formed prior to the active layer, and a lower surface of the active layer contacts the source and drain electrodes. The top-contact type is a form in which the active layer is formed prior to the source and drain electrodes, and an upper surface of the active layer contacts the source and drain electrodes.

The TFTs according to the invention can have various configurations besides the above configurations and may be appropriately provided with, for example, a protective layer on the active layer or an insulating layer on the substrate.

FIG. 1 shows a schematic cross-sectional view of a structure of a thin film transistor 1 according to a first embodiment of the invention, and FIG. 2 shows a schematic cross-sectional view of a structure of a thin film transistor 2 according to a second embodiment of the invention. In each of the thin film transistors 1 and 2 of FIGS. 1 and 2, the common elements are denoted by the same reference symbols.

The thin film transistor 1 according to the first embodiment shown in FIG. 1 is a bottom-gate and top-contact type transistor, and the thin film transistor 2 according to the second embodiment shown in FIG. 2 is a top-gate and bottom-contact type transistor. Although embodiments shown in FIGS. 1 and 2 are different in arrangement of a gate electrode 16, a source electrode 13, and a drain electrode 14, with respect to an oxide semiconductor layer 12, the elements denoted by the same reference symbols have the same functions, and the same material can be used for the elements.

Each of the thin film transistors 1 and 2 according to the embodiment of the invention has the gate electrode 16, a gate insulating film 15, the oxide semiconductor layer 12 (active layer), the source electrode 13, and the drain electrode 14, and the oxide semiconductor layer 12 includes, from a side closer to the gate electrode 16 in the film thickness direction, a first region A1 and a second region A2. The first region A1 and the second region A2 constituting the oxide semiconductor layer 12 are formed by the liquid phase method, respectively.

Hereinbelow, each of the constituent elements of the TFT according to the invention including a substrate on which the TFT 1 or 2 is to be formed is described in detail.

Substrate

The shape, structure, size and the like of the substrate 11 on which the thin film transistor 1 according to the invention is to be formed are not particularly limited and can be suitably selected depending on the purpose. The substrate 11 may have a single layer structure or a multi-layered structure.

Examples of the substrate 11 that can be used include an inorganic substrate such as glass or YSZ (yttrium-stabilized zirconia), a resin substrate, and a composite material thereof.

Specific examples of the substrate include: a substrate formed from a synthetic resin such as polybutylene terephthalate, polyethylene terephthalate, polyethylene naphthalate, polybutylene naphthalate, polystyrene, polycarbonate, polysulfone, polyether sulfone, polyarylate, allyl diglycol carbonate, polyamide, polyimide, polyamide-imide, polyetherimide, polybenzazole, polyphenylene sulfide, polycycloolefin, a norbornene resin, a fluorine resin such as polychlorotrifluoroethylene, a liquid crystal polymer, an acrylic resin, an epoxy resin, a silicone resin, an ionomer resin, a cyanate resin, a cross-linked fumaric acid diester, cyclic polyolefin, aromatic ether, maleimide-olefin, cellulose, and an episulfide compound; a composite plastic material with silicon oxide particles; a composite plastic material with metal nanoparticles, inorganic oxide nanoparticles, or inorganic nitride nanoparticles, or the like; a composite plastic material with a carbon fiber or a carbon nanotube; a composite plastic material with glass flakes, glass fibers, or glass beads; a composite plastic material with clay mineral or particles having a crystal structure derived from mica; a layered plastic material having at least one joint interface between thin glass and one of the above organic materials; a composite material having a barrier property and having at least one or more joint interfaces by alternately stacking an inorganic layer and an organic layer; a stainless substrate or a metal multilayer substrate in which stainless and dissimilar metal are layered; and an aluminum substrate and an aluminum substrate with an oxide film in which the surface is subjected to an oxidation treatment (for example, anodization treatment) to improve the insulation properties of the surface.

It is preferable that the resin substrate has excellent heat resistance, dimension stability, solvent resistance, electrical insulation properties, processability, low gas permeability, low hygroscopicity and the like. The resin substrate may be provided with a gas barrier layer to prevent transmission of moisture and oxygen, an under coat layer to enhance the flatness of the resin substrate and adhesiveness with a lower electrode, or the like.

Oxide Semiconductor Layer

The oxide semiconductor layer 12 (active layer) includes, from a side closer to the gate electrode 16, the first region A1 (sometimes referred to as "layer A1") and the second region A2 (sometimes referred to as "layer A2"), and is arranged facing the gate electrode 16 with the gate insulating film 15 provided therebetween. Both the layers of the first region A1 and the second region A2 are formed using a liquid phase method.

The first region A1 is represented by $In_{(a)}Ga_{(b)}Zn_{(c)}O_{(d)}$ ($a \geq 0$, $b \geq 0$, $c \geq 0$, $a+b+c=1$, $d > 0$) and is within a composition range satisfying $b \leq 1/3$ and $b \geq -10a/7+1$. Here, the upper limit of d is $d \leq 3/2$. On the other hand, the second region A2, which is located farther from the gate electrode 16 than the first region A1, i.e., on a side opposite to a surface of the first region A1 which contacts the gate insulating film 15, is represented by $In_{(e)}Ga_{(f)}Zn_{(g)}O_{(h)}$ ($e \geq 0$, $f \geq 0$, $g \geq 0$, $e+f > 0$, $h > 0$) and has a composition different from the first region A1. Here, the condition of $e+f+g=1$ is satisfied, and the upper limit of h is $h \leq 3/2$.

First Region

The first region A1 is represented by $In_{(a)}Ga_{(b)}Zn_{(c)}O_{(d)}$ ($a \geq 0$, $b \geq 0$, $c \geq 0$, $a+b+c=1$, $d > 0$) and is within a composition range satisfying $b \leq 1/3$ and $b \geq -10a/7+1$. From the viewpoint of stability against repeated driving, it is preferable that $b \geq 0$. From the viewpoint of achieving a higher mobility, the first region A1 is preferably within a composition range satisfying $b \leq a/2 - 1/10$ and $b \geq -3a/2 + 11/10$, and more preferably within a composition range further satisfying $b \geq 1/20$ and $c \geq 1/20$. In a case in which the first region A1 is within the above range, a higher electron field-effect mobility (1.4 cm$^2$/Vs or more) can be achieved.

The film thickness of the first region A1 is preferably less than 30 nm. It is preferable to use an extremely In-rich InGaZnO film, with which a higher mobility is easily achieved, for the first region A1. However, such a high mobility film has a high carrier concentration, and therefore there is a possibility that the threshold value is significantly negatively shifted. In a case in which the film thickness of the first region A1 is 30 nm or more, the total carrier concentration in the active layer becomes excessively high, and therefore pinch-off is relatively difficult.

The film thickness of the first region A1 is preferably 5 nm or more, from the viewpoints of obtaining the uniformity of the oxide semiconductor layer 12 and high mobility.

Second Region

The second region A2 in the oxide semiconductor layer 12 is arranged on a side farther from the gate electrode 16 than the first region A1, that is, on a side opposite to a surface of the first region A1 which contacts the gate insulating film 15. The second region A2 is an oxide semiconductor film represented by $In_{(e)}Ga_{(f)}Zn_{(g)}O_{(h)}$ ($e \geq 0$, $f \geq 0$, $g \geq 0$, $e+f > 0$, $h > 0$) and containing at least one of In or Ga.

The composition of the second region A2 preferably satisfies f/(e+f)>0.25. In a case in which the composition of the second region A2 is within a range satisfying f/(e+f) >0.25, excessive carrier inflow into the first region A1 and channel formation in the second region can be suppressed, and negative-shift of the threshold voltage (Vth) can be effectively suppressed.

The composition of the second region A2 preferably satisfies f/(e+f)<0.875. In a case in which the composition of the second region A2 satisfies f/(e+f)<0.875, an increase in resistance of the second region due to an increase in the Ga content can be suppressed and high mobility can be achieved.

The film thickness of the second region A2 is preferably 30 nm or more. In a case in which the film thickness of the second region A2 is 30 nm or more, reliable reduction in off-current can be expected. On the other hand, in a case in which the film thickness of the second region A2 is 10 nm or less, an increase in off-current and deterioration in S value may be caused. The film thickness of the second region A2 is preferably less than 70 nm. In a case in which the film thickness of the second region A2 is 70 nm or more, reduction in off-current can be expected. However, the resistance between the source and drain electrodes and the first region A1 is increased, as a result of which mobility may be decreased. Therefore, the film thickness of the second region A2 is preferably more than 10 nm and less than 70 nm.

It is noted that the film thickness of each of the first region A1 and the second region A2 can be controlled, for example, by adjusting the rotation number during spin coating.

Entire Oxide Semiconductor Layer

The film thickness of the entire oxide semiconductor layer 12 (total film thickness) is preferably from about 10 nm to about 200 nm, and more preferably 35 nm or more and less than 80 nm, from the viewpoints of the uniformity and patterning property of the film.

The oxide semiconductor layer 12 (first region A1, second region A2) is preferably amorphous. In a case in which each of the layers of the first region A1 and the second region A2 is amorphous, there is no crystal grain boundary, and a film having an improved uniformity can be obtained.

Whether the multi-layered film including the first and second regions A1 and A2 is amorphous can be confirmed by X-ray diffraction measurement. That is, when a clear peak showing a crystal structure is not detected by the X-ray diffraction measurement, it can be confirmed that the multi-layered film is amorphous.

Source and Drain Electrodes

The material and the structure for the source electrode 13 and the drain electrode 14 are not particularly limited as long as they have a high conductivity. The source electrode 13 and the drain electrode 14 can be formed by forming a single layer or a layered structure having two or more layers from, for example, metal such as Al, Mo, Cr, Ta, Ti, Au, or Ag; Al—Nd; and/or a metal oxide such as tin oxide, zinc oxide, indium oxide, indium tin oxide (ITO), or indium zinc oxide (InZnO).

In a case in which the source electrode 13 and the drain electrode 14 are formed from the above metal or metal oxide, the thickness thereof is preferably from 10 nm to 1000 nm, and more preferably from 50 nm to 100 nm, in consideration of film formation property, patterning property by etching or a lift-off method, and conductivity.

Gate Insulating Film

The gate insulating film 15 is a layer spacing the gate electrode 16 from the oxide semiconductor layer 12 and the source and drain electrodes 13 and 14, in an insulating state, and preferably has high insulation properties. The gate insulating film 15 can be formed from, for example, $SiO_2$, SiNx, SiON, $Al_2O_3$, $Y_2O_3$, $Ta_2O_5$, or $HfO_2$, or two or more kinds of these compounds.

Although the gate insulating film 15 is required to have a sufficient thickness to reduce a leak current and to enhance voltage resistance, there is a possibility that a drive voltage is increased when the thickness is too large. The thickness of the gate insulating film 15 depends on the material, and preferably from 10 nm to 10 μm, more preferably from 50 nm to 1000 nm, and still more preferably from 100 nm to 400 nm.

Gate Electrode

The gate electrode 16 is not particularly limited as long as it has high conductivity. The gate electrode 16 can be formed by forming a single layer or a layered structure having two or more layers from, for example, metal such as Al, Mo, Cr, Ta, Ti, Au, or Ag; Al—Nd; and/or a metal oxide such as tin oxide, zinc oxide, indium oxide, indium tin oxide (ITO), or indium zinc oxide (InZnO).

In a case in which the gate electrode 16 is formed from the above metal or metal oxide, the thickness is preferably from 10 nm to 1000 nm, and more preferably from 50 nm to 200 nm, in consideration of film-formation property, patterning property by etching or a lift-off method, and conductivity.

Method of Producing Thin Film Transistor

Hereinbelow, a method according to the invention that produces a bottom-gate and top contact type thin film transistor 1 shown in FIG. 1 is explained. In the following explanation, constituent material and thickness of respective members are the same as described above, and therefore the description is omitted to avoid redundant description.

Formation of Gate Electrode

First, the substrate 11 is provided, and then a layer other than the thin film transistor 1 is formed on the substrate 11 if necessary, followed by the formation of the gate electrode 16.

The gate electrode 16 may be formed in accordance with a method suitably selected from, for example, a printing method; a wet method such as a coating method; a physical method such as a vacuum deposition method, a sputtering method, or an ion plating method; or a chemical method such as CVD or plasma CVD method, in consideration of compatibility with a material to be used. For example, after an electrode film is formed, a patterning is performed so as to have a certain form by etching or a lift-off method, thereby forming the gate electrode 16. At that time, it is preferable that the gate electrode 16 and a gate wiring are subjected to patterning simultaneously.

Formation of Gate Insulating Film

After the formation of the gate electrode 16, the gate insulating film 15 is formed.

The gate insulating film 15 may be formed in accordance with a method suitably selected from a printing method; a wet method such as a coating method; a physical method such as a vacuum deposition method, a sputtering method, an ion plating method; or a chemical method such as CVD or plasma CVD method, in consideration of compatibility with a material to be used. For example, the gate insulating film 15 may be subjected to patterning by photolithography or etching so as to have a certain shape.

Formation of Oxide Semiconductor Layer

Subsequently, the layers of the first region A1 and the second region A2 which constitutes the oxide semiconductor layer 12 are formed in this order at a position facing the gate electrode 16 on the gate insulating film 15.

The order of forming the first region A1 and the second region A2 may be determined based on the position thereof relative to the gate electrode 16. For example, when producing the bottom gate-type thin film transistor 1 shown in FIG. 1, the oxide semiconductor layer 12 is obtained by forming the first region A1 and the second region A2 in this order. On the other hand, when producing the top-gate type thin film transistor 2 shown in FIG. 2, the oxide semiconductor layer 12 is obtained by forming the second region A2 and the first region A1 in this order.

First, a raw material solution including a solvent and a metal organic compound including an organic component and a metal element for forming each of regions A1 and A2 of the oxide semiconductor layer 12 is prepared. A first oxide precursor film including the organic component and at least In is formed on the substrate 11 with the gate insulating film 15 provided thereon by the liquid phase method such as spin coating, bar coating, dip coating, spray coating, inkjetting, dispensing, screen printing, relief printing, or intaglio printing. Thereafter, a second oxide precursor layer is formed on the first oxide precursor layer by the liquid phase method in a similar manner.

The raw material solution used for forming each of the first and second oxide precursor films by the liquid phase method is not particularly limited as long as it has an intended composition when formed into the first region A1 or the second region A2. For example, a raw material solution including a solvent and at least one selected from a metal alkoxide, β-diketone complex, or a nitrate may be used.

For example, a raw material solution including a metal organic compound that can be thermally decomposed in a temperature region of 500° C. or less to form an oxide is preferably used. It is more preferable to use a solution including a metal alkoxide or an organic acid salt that contains a metal element for constituting an intended oxide semiconductor. In a case in which the solution containing a metal alkoxide or an organic acid salt is used, a process of removing impurity substances such as nitric acid or chlorine, which may be generated when using a nitrate or a chloride, is not necessary, and the generation of harmful gases can be suppressed.

Organic Acid Salt

Examples of the organic acid salt include a β-diketone complexing group, a β-keto carboxylic acid ester complexing group, a β-ketocarboxylic acid complexing group, and a ketooxy group (a ketooxy complexing group).

Specific examples of the β-diketone complexing group include 2,4-pentanedione (also referred to as acetyl acetone or acetoacetone), 1,1,1,5,5,5-hexamethyl-2,4-pentanedione, 2,2,6,6-tetramethyl-3,5-heptanedione, and 1,1,1-trifluoro-2,4-pentanedione.

In a case in which a β-diketone complex is used as a material for forming the oxide precursor film, it is preferable to use β-diketone as a solvent.

Specific examples of the β-ketocarboxylic acid ester complexing group include methyl acetoacetate, ethyl acetoacetate, propyl acetoacetate, ethyl trimethylacetoacetate, and methyl trifluoroacetoacetate.

Specific examples of the β-ketocarboxylic acid include acetoacetic acid, and trimethylacetoacetic acid.

Specific examples of the ketooxy group include an acetooxy group (or an acetoxy group), a propionyloxy group, a butyryloxy group, an acryloyloxy group, and a methacryloyloxy group. The carbon atom number of these groups is preferably 18 or less. These groups may be straight-chained or branched, and may be those in which the hydrogen atom is substituted with a fluorine atom.

Metal Alkoxide

The metal alkoxide solution to be used may be a solution including at least a metal alkoxide compound represented by the following Formula (I).

$$M(OR)n \qquad (I)$$

In Formula (I), M represents In, Ga, or Zn; R represents an organic group; and n represents an integer of 1 or more.

The metal alkoxide used in the invention may be present separately, or part of the metal alkoxide may be linked to one another to form a complex alkoxide.

The metal alkoxide solution preferably has a viscosity of from 1 mPa·s to 100 mPa·s. Each of the organic groups represented by R in Formula (I) may be the same as or different from one another for all of the metal elements, and represents preferably an alkyl group having from 1 to 20 carbon atoms, and more preferably an alkyl group having from 1 to 6 carbon atoms.

Specific examples of the metal alkoxide corresponding to Formula (I) include zinc ethoxide, zinc ethoxyethoxide, zinc dimethylaminoethoxide, zinc methoxyethoxide, indium isopropoxide, indium n-butoxide, indium methoxyethoxide, indium diethylaminoethoxide, gallium ethoxide, and gallium isopropoxide.

In the metal alkoxide solution, the total mass concentration of all of the metal alkoxides is preferably from 0.5% by mass to 20% by mass, and more preferably from 1% by mass to 10% by mass. In a case in which the total content of the metal alkoxides is less than 0.5% by mass, there is a possibility that a uniform thin film cannot be formed, and when the total content of the metal alkoxides exceeds 20% by mass, there is a possibility that a sufficiently thin film cannot be constituted.

The metal alkoxide solution contains an appropriate solvent for dissolving the metal alkoxide compound. Examples of the solvent include water, alcohols, amino alcohols, and glycols. From the viewpoints of solubility, wettability, a somewhat high boiling point, and suppressing hydrolysis in a solution, amino alcohols are preferable. From the viewpoints of stability and drying property of the dispersion, it is more preferable that the metal alkoxide solution contains at least one high boiling point solvent.

The boiling point of the high boiling point solvent is, for example, from 120° C. to 250° C. From the viewpoint of reducing the burden at the time of drying, the boiling point is preferably from 130° C. to 200° C. In a case in which the boiling point is lower than 120° C., the drying speed is fast so that sufficient smoothness is less likely to be obtained; and in a case in which the boiling point exceeds 250° C., the solvent is prone to remain during the formation of a thin film.

Specific examples of the high boiling point solvent include 2-ethoxyethanol, 2-(methoxyethoxy)ethanol, 2-(ethoxyethoxy)ethanol, 2-isopropoxyethanol, 1-ethoxy-2-propanol, 2-diethylaminoethanol, 2-dipropylaminoethanol, cyclohexanol, ethylene glycol, diethylene glycol, and benzyl alcohol.

Furthermore, the metal alkoxide solution may be used as a solution for coating, after adding various additives such as an antistatic agent, a plasticizer, a polymer binder, a thickener, or the like, depending on the purpose to adjust physical properties.

It is preferable that the oxide precursor film formed by the liquid phase method is subjected to a treatment to improve film density. Specific examples thereof include a photo treatment process and a plasma treatment process, and, from the viewpoint of treatment costs, the photo treatment process is preferable. In the photo treatment process, it is preferable to irradiate the oxide precursor film with ultraviolet rays. The ultraviolet rays can easily change the binding state of organic components in the film, and therefore improvement in film density can be expected. Examples of the light source that can be used include a low pressure mercury lamp, a deuterium lamp, a xenon excimer lamp, a metal halide lamp, and an excimer laser.

The treatment to improve film density may be performed after each of the formation of the first oxide precursor film and the formation of the second oxide precursor film, or may be performed after the formation of all of the oxide precursor films.

In order to remove the organic component remaining in the oxide precursor film, a heat treatment is conducted. The method for the heat treatment is not particularly limited, and examples thereof include a method of heating using an electric furnace or a muffle furnace, and a lamp or hot plate heating method.

The heat treatment temperature may be equal to or higher than the thermal decomposition temperature of the metal organic compound to be used. For example, when the metal alkoxide or the β-diketone complex is used, it is preferable to conduct the heat treatment at 400° C. or higher.

The heat treatment temperature is preferably 600° C. or lower. In a case in which the heat treatment temperature exceeds 600° C., the metal elements are significantly diffused between the first and second oxide films and it becomes difficult to maintain the layered structure.

The thermal decomposition temperature varies with the structure of the complex, and can be evaluated, for example, based on the thermogravimetry (TG).

After the heat treatment, the oxide semiconductor layer 12 is subjected to patterning. Patterning may be performed by photolithography and etching. Specifically, a resist pattern is formed at portions that should remain by photolithography, and then etching is performed using an acid solution such as hydrochloric acid, nitric acid, dilute sulfuric acid, or a mixed liquid of phosphoric acid, nitric acid, and acetic acid, thereby forming a pattern of the oxide semiconductor layer 12.

Alternatively, patterning of the oxide semiconductor layer 12 may be performed before the heat treatment process, and then the heat treatment process may be carried out.

Through the above processes, the oxide semiconductor layer 12 having the first region A1 and the second region A2, each of which is constituted by the oxide semiconductor, can be formed by the liquid phase method.

It is noted that the raw material for forming the oxide semiconductor layer 12 in the invention is not limited to the metal alkoxide or the organic acid salt, and, for example, the raw material may be a nitrate. The use of the nitrate as the raw material has the advantage in that the contamination by a carbon component, which may form an impurity during film formation, can be suppressed, compared to the case of using the metal alkoxide or the organic acid salt.

Furthermore, the nitrate has generally a lower thermal decomposition temperature (approximately 250° C.) than the metal alkoxide or the organic acid salt, and therefore high TFT properties can be realized at a lower temperature.

Formation of Source Electrode and Drain Electrode

Subsequently, a metal film used for the formation of the source and drain electrodes 13 and 14 is formed on the oxide semiconductor layer 12.

Both the source electrode 13 and the drain electrode 14 may be formed in accordance with a method appropriately selected from, for example, a wet method such as a printing method or a coating method; a physical method such as a vacuum deposition method, a sputtering method, or an ion plating method; or a chemical method such as CVD or a plasma CVD method, in consideration of a compatibility with a material to be used.

For example, the metal film is subjected to patterning to have a certain shape by etching or a lift-off method to form the source electrode 13 and the drain electrode 14. At this time, it is preferable that patterning of the source electrode 13, the drain electrode 14, and wirings (not shown) connected to the source electrode 13 and the drain electrode 14 is performed simultaneously.

The thin film transistor 1 having a constitution shown in FIG. 1 can be produced by the above procedures.

The thin film transistor produced according to the invention can be produced at a relatively low temperature by the liquid phase method and exhibits high mobility ($\geq 1$ cm$^2$/Vs), and therefore can be applied to various devices. Both the display device and the sensor using the thin film transistor produced according to the invention exhibit favorable characteristics with low power consumption. The "characteristics" referred to herein are the display characteristics in the case of the display device and the sensitivity characteristics in the case of the sensor.

Liquid Crystal Display Device

Figure 3:
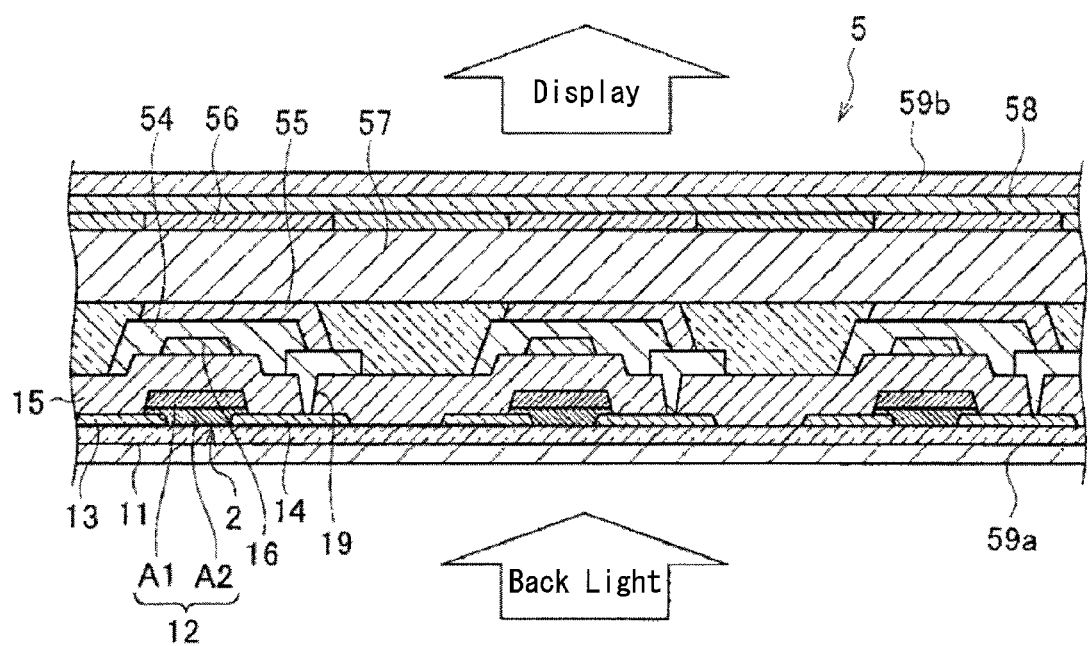
FIG. 3 shows a schematic cross-sectional view of a part of a liquid crystal display device according to an embodiment.
Figure 4:
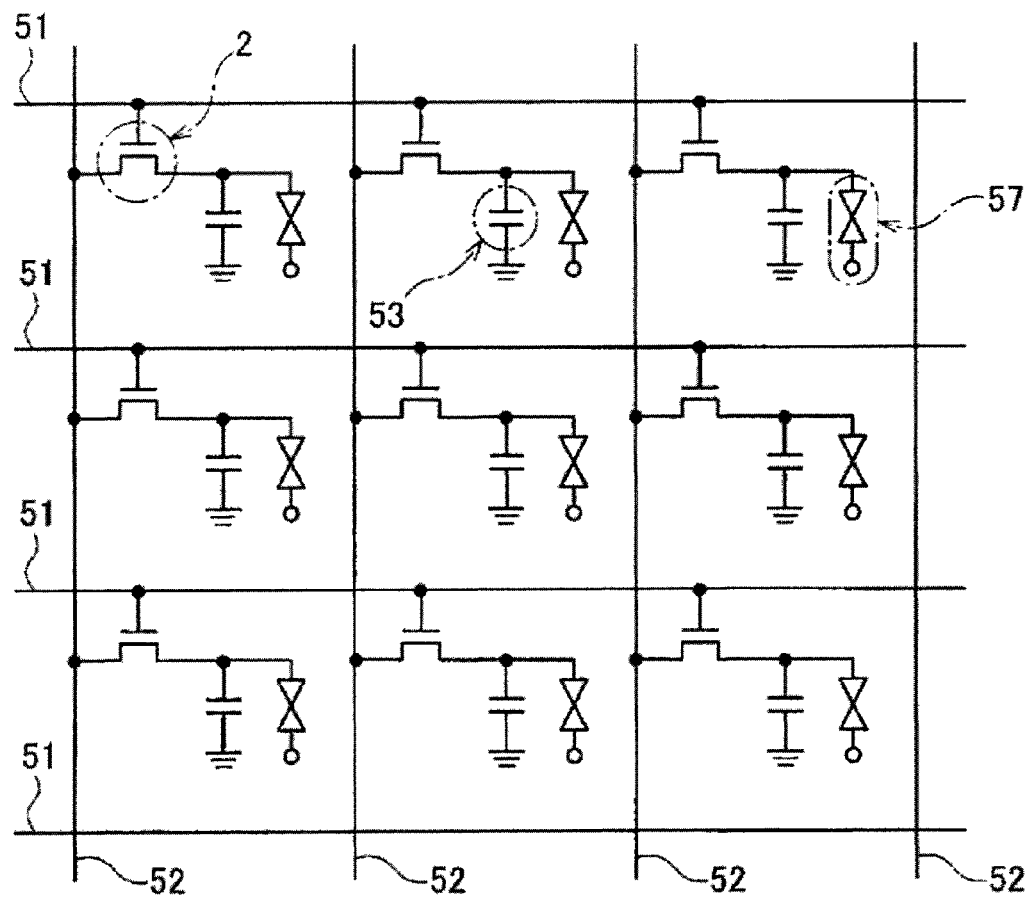
FIG. 4 shows a schematic configuration view of electrical wiring in the liquid crystal display device of FIG. 3.

FIG. 3 shows a schematic cross-sectional view of a part of a liquid crystal display device as one embodiment of a display device provided with the thin film transistor produced according to the invention, and FIG. 4 shows a schematic configuration diagram of electrical wiring thereof.

As shown in FIGS. 3 and 4, a liquid crystal display device 5 of the embodiment is provided with a top gate and bottom-contact type thin film transistor 2 as shown in FIG. 2, and on the gate electrode 16, which is protected by a passivation layer 54, of the thin film transistor 2, a liquid crystal layer 57 which is interposed between a pixel lower electrode 55 and an upper electrode 56 facing thereto, and an RGB color filter 58 for forming different colors corresponding to the respective pixels; and further provided with polarizing plates 59a and 59b on the substrate 11 side of the TFT 2 and on the color filter 58, respectively. The top-gate and bottom contact type thin film transistor 2 includes an oxide semiconductor layer 12, and the oxide semiconductor layer 12 includes, from a side closer to the gate electrode 16 in the film thickness direction, the first region A1 and the second region A2.

As shown in FIG. 4, the liquid crystal display device 5 of the embodiment is provided with plural gate wirings 51 parallel to one another and data wirings 52 which intersect the gate wirings 51 and which are parallel to one another. Here, the gate wiring 51 and the data wiring 52 are electrically insulated. The thin film transistor 2 is provided near the intersection part of the gate wiring 51 and the data wiring 52.

As shown in FIGS. 3 and 4, the gate electrode 16 of the thin film transistor 2 is connected to the gate wiring 51, and the source electrode 13 of the thin film transistor 2 is connected to the data wiring 52. The drain electrode 14 of the thin film transistor 2 is electrically connected to the pixel lower electrode 55 through a contact hole 19 provided in the gate insulating film 15 (in which a conductor is embedded in the contact hole 19). The pixel lower electrode 55 and the grounded upper electrode 56 facing thereto form a capacitor 53.

Although the liquid crystal device of the embodiment shown in FIG. 3 is provided with the top-gate type thin film transistor, the thin film transistor used in the liquid crystal device as the display device according to the invention is not limited to the top-gate type thin film transistor, and a bottom gate type-thin film transistor may be used.

Since the thin film transistor produced according to the invention has high mobility, high quality display such as high definition, high-speed response, and high contrast can be realized in the liquid display device and it is suitable for an increase in size of a screen. In particular, when the active layer (oxide semiconductor layer) 12 is amorphous, variation in element characteristics can be suppressed, and an excellent display quality without unevenness in a large display screen is realized. Furthermore, since characteristic shift is small, the gate voltage can be reduced, and, furthermore, the power consumption of the display device can be reduced.

According to the invention, since the first region A1 and the second region A2 constituting the active layer can be formed using an amorphous film that can be formed at a low temperature (for example, 200° C. or less), a resin substrate (plastic substrate) can be used as a substrate. Accordingly, according to the invention, a flexible liquid crystal display device which is excellent in display quality can be provided.

Organic EL Display Device

Figure 5:
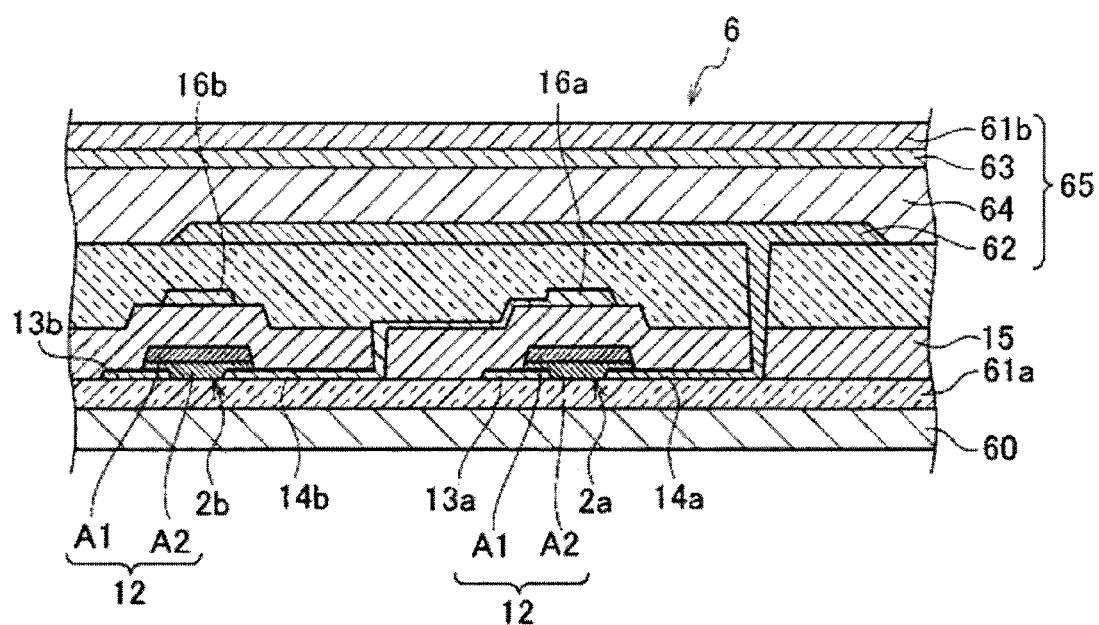
FIG. 5 shows a schematic cross-sectional view of a part of an organic EL display device according to an embodiment.
Figure 6:
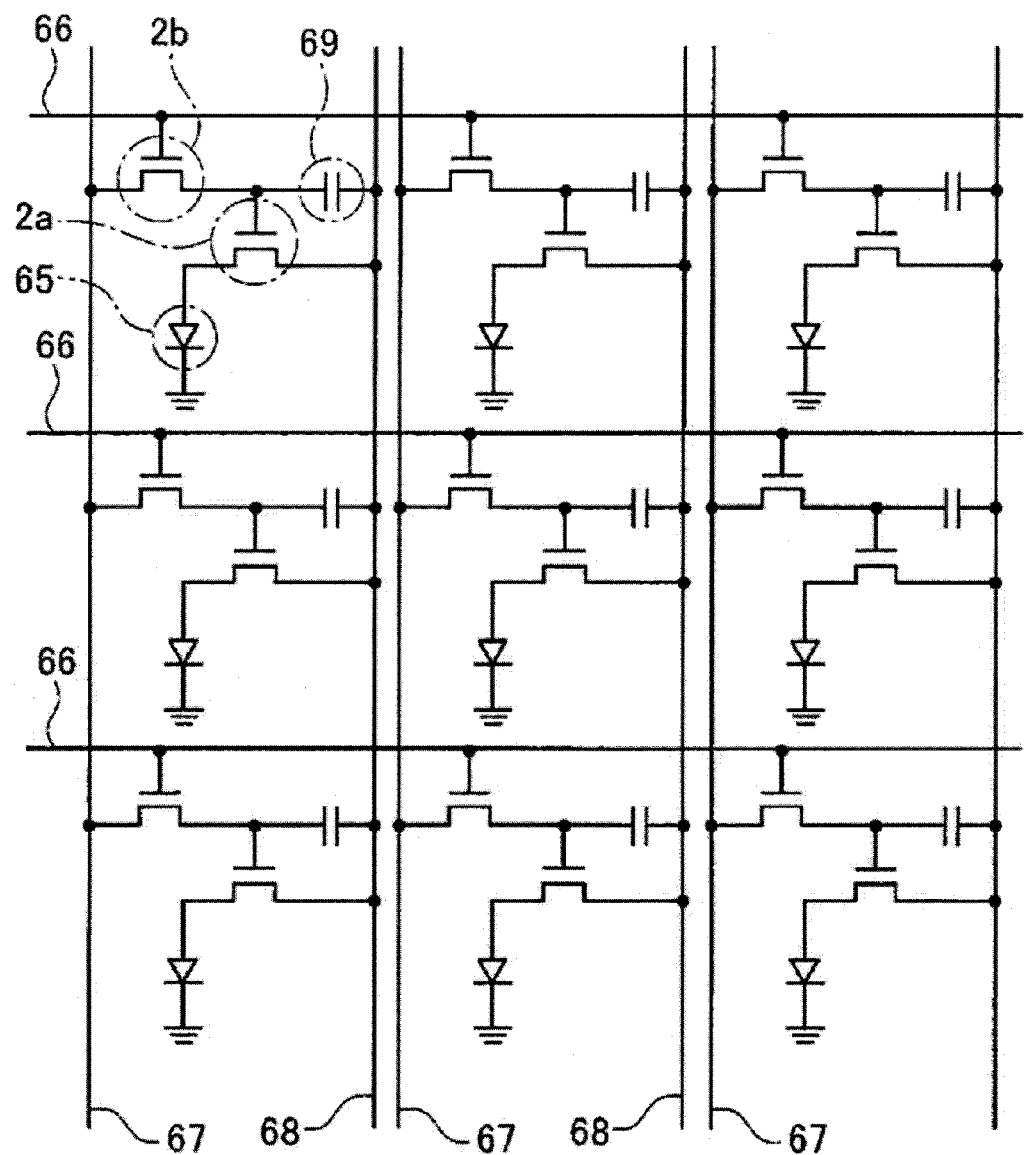
FIG. 6 shows a schematic configuration view of electrical wiring in the organic EL display device of FIG. 5.

As one embodiment of the display device provided with the TFT produced according to the invention, FIG. 5 shows a schematic cross-sectional view of a part of an active matrix type-organic EL display device, and FIG. 6 shows a schematic configuration diagram of electrical wiring thereof.

As a system of driving the organic EL display device, there are two kinds of systems, a simple matrix system and an active matrix system. Although the simple matrix system has an advantage in terms of production at low cost, a pixel is made to emit light by selecting every one scanning line, and therefore the emission time per one scanning line is inversely proportional to the number of scanning lines. Thus, it is difficult to realize high definition and a large display screen. In the active matrix system, the production cost is high since a transistor and a capacitor are formed for every pixel. However, there is no problem that the number of scanning lines cannot be increased as in the case of the simple matrix system, and therefore the active matrix system is suitable for realizing high definition and a large size screen.

In the active matrix type organic EL display device 6 of the embodiment, top-gate and top-contact type thin film transistors are provided on a passivation layer 61a on a substrate 60, as a driving TFT 2a and a switching TFT 2b, respectively. Above the driving thin film transistor 2a and the switching thin film transistor 2b, an organic light emitting element 65 which includes an organic light emitting layer 64 placed between a lower electrode 62 and an upper electrode 63 is provided, and the upper surface thereof is protected by a passivation layer 61b. Each of the driving thin film transistor 2a and the switching thin film transistor 2b has the oxide semiconductor layer 12, and each oxide semiconductor layer 12 includes, from a side closer to each gate electrode 16a or 16b in the film thickness direction, the first region A1 or the second region A2.

As shown in FIGS. 5 and 6, the organic EL display device 6 of the embodiment is provided with plural gate wirings 66 parallel to one another and data wirings 67 and driving wirings 68 which intersect the gate wirings 66 and are parallel to one another. Here, the gate wiring 66 is electrically insulated from the data wiring 67 and the driving wiring 68. The gate electrode 16b of the switching thin film transistor 2b is connected to the gate wiring 66, and the source electrode 13b of the switching thin film transistor 2b is connected to the data wiring 67. The drain electrode 14b of the switching thin film transistor 2b is connected to the gate electrode 16a of the driving thin film transistor 2a, and the driving thin film transistor 2a is kept in an on-state by using a capacitor 69. The source electrode 13a of the driving thin film transistor 2a is connected to the driving wiring 68, and the drain electrode 14a is connected to an organic EL light emitting element 65.

Although the organic EL device of the embodiment shown in FIG. 5 is one provided with the top-gate type driving thin film transistor 2a and the top-gate type switching thin film transistor 2b, the thin film transistor used in the organic EL device as the display device according to the invention is not limited to the top-gate type thin film transistor, and may be a bottom-gate type thin film transistor.

Since the thin film transistor produced according to the invention has high mobility, low power consumption and high quality display can be realized. According to the invention, the first region A1 and the second region A2 constituting the active layer can be formed using an amorphous film that can be formed at a relatively low temperature, and therefore a resin substrate (plastic substrate) can be used as a substrate. Therefore, according to the invention, an organic EL display device which is flexible and excellent in display quality can be provided.

In the organic EL display device shown in FIG. 5, the upper electrode 63 may be a transparent electrode to produce a top-emission type organic EL display device, or each of the lower electrode 62, the electrode of the driving thin film transistor 2a, and the electrode of the switching thin film transistor 2b may be a transparent electrode to produce a bottom-emission type organic EL display device.

X-Ray Sensor

Figure 7:
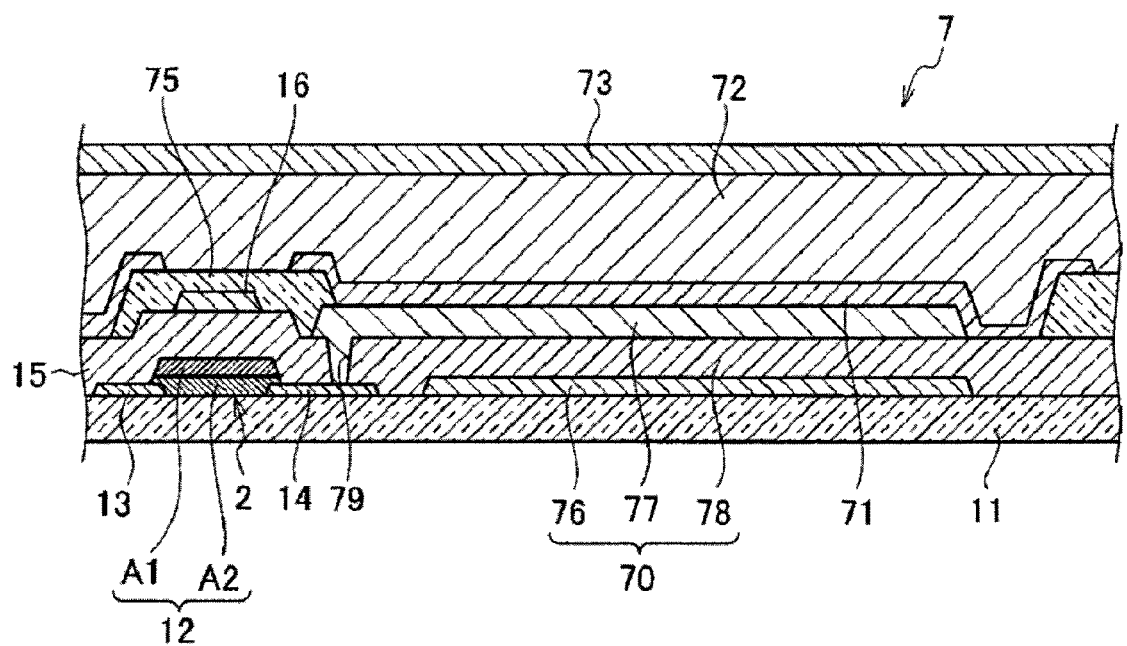
FIG. 7 shows a schematic cross-sectional view of a part of an X-ray sensor array according to an embodiment.
Figure 8:
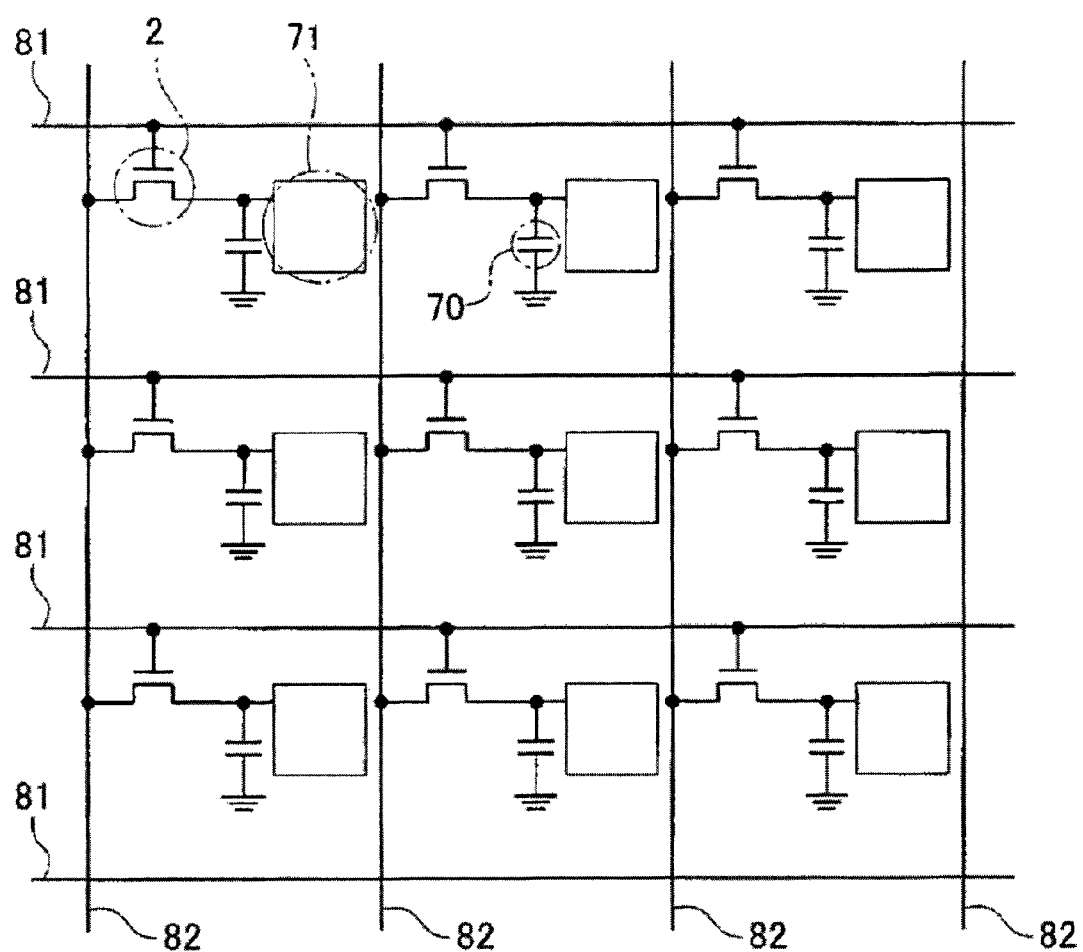
FIG. 8 shows a schematic configuration view of electrical wiring in the X-ray sensor array of FIG. 7.

FIG. 7 shows a schematic cross-sectional view of a part of an X-ray sensor as one embodiment of the sensor according to the invention, and FIG. 8 shows a schematic configuration diagram of electrical wiring thereof.

An X-ray sensor 7 of the embodiment is configured to include the thin film transistor 2 and the capacitor 70 formed on the substrate 11, and a charge collecting electrode 71 formed on the capacitor 70, an X-ray conversion layer 72, and an upper electrode 73. A passivation film 75 is provided on the thin film transistor 2.

The capacitor 70 has a structure in which a lower electrode for capacitor 76 and an upper electrode for capacitor 77 hold an insulating film 78 therebetween. The upper electrode for capacitor 77 is connected to one of the source electrode 13 and the drain electrode 14 of the thin film transistor 2 (the drain electrode 14 in FIG. 7) through a contact hole 79 provided between the insulating film 78 and the gate insulating film 15. The thin film transistor 2 includes the oxide semiconductor layer 12, and the oxide semiconductor layer 12 includes, from a side closer to the gate electrode 16 in the film thickness direction, the first region A1 and the second region A2.

The charge collecting electrode 71 is provided on the upper electrode for capacitor 77 in the capacitor 70 and contacts the upper electrode for capacitor 77. The X-ray conversion layer 72 is formed from amorphous selenium and provided so as to cover the thin film transistor 2 and the capacitor 70. The upper electrode 73 is provided on the X-ray conversion layer 72 and contacts the X-ray conversion layer 72.

As shown in FIG. 8, the X-ray sensor 7 of the embodiment is provided with plural gate wirings 81 parallel to one another and plural data wirings 82 which intersect the gate wirings 81 and are parallel to one another. Here, the gate wiring 81 and the data wiring 82 are electrically insulated. The thin film transistor 2 is provided near the intersection part of the gate wiring 81 and the data wiring 82.

The gate electrode 16 of the thin film transistor 2 is connected to the gate wiring 81, and the source electrode 13 of the thin film transistor 2 is connected to the data wiring 82. The drain electrode 14 of the thin film transistor 2 is connected to the charge collecting electrode 71, and the charge collecting electrode 71 and the grounded lower electrode for capacitor 76 forms the capacitor 70.

In the X-ray sensor 7 in the present configuration, an X ray is irradiated from an upper portion (the upper electrode 73 side) in FIG. 7, and an electron-hole pair is generated in the X-ray conversion layer 72. When a high electric field is applied to the X-ray conversion layer 72 by the upper electrode 73, generated electric charges are accumulated in the capacitor 70 and read-out is performed by scanning the thin film transistor 2 in sequence.

Since the X-ray sensor according to the invention is provided with the thin film transistor 2 having a high on-current and an excellent reliability, S/N is high and sensitivity characteristics are excellent. Therefore, in a case in which the X-ray sensor is used in an X-ray digital imaging device, an image with wide dynamic range is obtained.

In particular, it is preferable that the X-ray digital imaging device according to the invention is not only capable of taking a still image but also capable of performing fluoroscopy for moving images and taking a still image with a single X-ray digital imaging device. Furthermore, in a case in which the first region A1 and the second region A2 forming the active layer in the thin film transistor 2 are amorphous, an image having an excellent uniformity is obtained.

Although the X-ray sensor of the embodiment shown in FIG. 7 is provided with the top-gate type thin film transistor, the thin film transistor used in the sensor according to the invention is not limited to the top-gate type thin film transistor, and may be a bottom gate type-thin film transistor.

EXAMPLES

Hereinbelow, the Examples are described, but the invention is not limited to the Examples.

Example 1

Preparation of First and Second Oxide Precursor Films Using Metal Alkoxide 1.32 g of zinc acetate dihydrate, 0.75 g of gallium isopropoxide, and 5.79 g of indium isopropoxide were weighed, and were added to 100 mL of diethylethanolamine. The mixture was then stirred at a temperature of 150° C., thereby obtaining a light-yellow first metal alkoxide-based raw material liquid. Here, the raw material liquid was prepared to have the metal composition ratio of In:Ga:Zn=0.7:0.1:0.2 when formed into a film.

In a similar manner, 2.20 g of zinc acetate dihydrate, 3.73 g of gallium isopropoxide, and 1.38 g of indium isopropoxide were weighed, and were added to 100 mL of diethylethanolamine. The mixture was then stirred at a temperature of 150° C., thereby obtaining a light-yellow second metal alkoxide-based raw material liquid. Here, the raw material liquid was prepared to have the metal composition ratio of In:Ga:Zn=1/6:3/6:2/6 when formed into a film.

On a p-type silicon substrate with a thermally oxidized film, the first metal alkoxide-based raw material liquid was spin-coated at a speed of 3000 rpm, and was air dried for 5 minutes, thereby forming a first oxide precursor film having a film thickness of 35 nm.

Subsequently, the second metal alkoxide-based raw material liquid was spin-coated at a speed of 3000 rpm, and was air dried for 5 minutes. The spin coating and air drying were repeated two times, thereby forming a second oxide precursor film having a film thickness of 70 nm.

The obtained oxide precursor layered film was subjected to a heat treatment in a box furnace at 450° C. for 1 hour.

In this manner, a simplified TFT for evaluation was prepared. The thicknesses of the first region A1 and the second region A2, constituting the oxide semiconductor layer, were 25 nm and 50 nm, respectively.

Example 2

Preparation of First and Second Oxide Precursor Films Using β-Diketone Complex 4.32 g of indium acetylacetone, 0.551 g of gallium acetylacetone, and 0.791 g of zinc acetylacetone were weighed, and were added to 100 mL of acetylacetone. The mixture was then stirred at room temperature, thereby obtaining a colorless first metal β-diketone-based raw material liquid. Here, the raw material liquid was prepared to have the metal composition ratio of In:Ga:Zn=0.7:0.1:0.2 when formed into a film.

In a similar manner, 1.03 g of indium acetylacetone, 2.75 g of gallium acetylacetone, and 1.32 g of zinc acetylacetone were weighed, and were added to 100 mL of acetylacetone. The mixture was then stirred at room temperature, thereby obtaining a colorless second metal β-diketone-based raw material liquid. Here, the raw material liquid was prepared to have the metal composition ratio of In:Ga:Zn=1/6:3/6:2/6 when formed into a film.

On a p-type silicon substrate with a thermally oxidized film, the first metal β-diketone-based raw material liquid was spin-coated at a speed of 3000 rpm, and was air dried for 5 minutes, thereby forming a first oxide precursor film having a film thickness of 35 nm.

Subsequently, the second metal β-diketone-based raw material liquid was spin-coated at a speed of 3000 rpm, and was air dried for 5 minutes. The spin coating and air drying were repeated two times, thereby forming a second oxide precursor film having a film thickness of 70 nm.

The obtained oxide precursor layered film was subjected to a heat treatment in a box furnace at 450° C. for 1 hour.

In this manner, a simplified TFT for evaluation was prepared. The thicknesses of the first region A1 and the second region A2, constituting the oxide semiconductor layer, were 25 nm and 50 nm, respectively.

Composition Dependency in First Region

How the composition of the first region influences the TFT characteristics was evaluated by changing the ratio of the charged raw materials for the first region and using the method similar to Example 1. The ratio of the charged raw materials for the second region was fixed such that the second region has the metal composition ratio of In:Ga:Zn=1/6:3/6:2/6 when formed into a film.

The metal composition ratio when formed into a film was confirmed using X-ray fluorescence (XRF) spectrometer.

With regard to the TFT thus produced, a mobility μ was measured using a semiconductor parameter analyzer 4156C (manufactured by Agilent Technologies, Inc.). The linear mobility was calculated from Vg-Id characteristics in the linear region obtained by changing the gate voltage (Vg) within a range of from −30 V to +30V at a fixed drain voltage (Vd) of 1 V.

The mobility in the case of changing the composition of the first region is summarized in the following Table 1. With regard to respective TFTs, the composition range and mobility of the first region A1 is shown in FIG. 9 by the ternary phase diagram.

TABLE 1

| | Cationic composition of first region | | | Electron field-effect mobility (cm²/Vs) |
|---|---|---|---|---|
| | a | b | c | |
| Example 1 | 7/10<br>0.700 | 1/10<br>0.100 | 2/10<br>0.200 | 1.71 |
| Example 2 | 8/10<br>0.800 | 1/10<br>0.100 | 1/10<br>0.100 | 2.12 |
| Example 3 | 14/20<br>0.700 | 5/20<br>0.250 | 1/20<br>0.050 | 1.52 |
| Example 4 | 6/10<br>0.60 | 2/10<br>0.20 | 2/10<br>0.20 | 1.48 |
| Example 5 | 18/20<br>0.900 | 1/20<br>0.050 | 1/20<br>0.050 | 2.49 |
| Example 6 | 14/20<br>0.700 | 1/20<br>0.050 | 5/20<br>0.250 | 1.64 |
| Example 7 | 7/10<br>0.700 | 0<br>0 | 3/10<br>0.300 | 1.21 |
| Example 8 | 7/15<br>0.467 | 5/15<br>0.333 | 3/15<br>0.200 | 1.09 |
| Example 9 | 37/60<br>0.617 | 20/60<br>0.333 | 3/60<br>0.050 | 1.15 |
| Comparative Example 1 | 2/3<br>0.667 | 0<br>0 | 1/3<br>0.333 | 0.80 |
| Comparative Example 2 | 4/10<br>0.400 | 4/10<br>0.400 | 2/10<br>0.200 | 0.54 |
| Comparative Example 3 (single film, 450° C.) | 1/3<br>0.333 | 1/3<br>0.333 | 1/3<br>0.333 | 0.003 |
| Comparative Example 4 (single film, 600° C.) | 1/3<br>0.333 | 1/3<br>0.333 | 1/3<br>0.333 | 0.05 |
| Comparative Example 5 | 3/10<br>0.300 | 2/10<br>0.200 | 5/10<br>0.500 | 0.001 |
| Comparative Example 6 | 5/10<br>0.500 | 1/10<br>0.100 | 4/10<br>0.400 | 0.43 |

Figure 9:
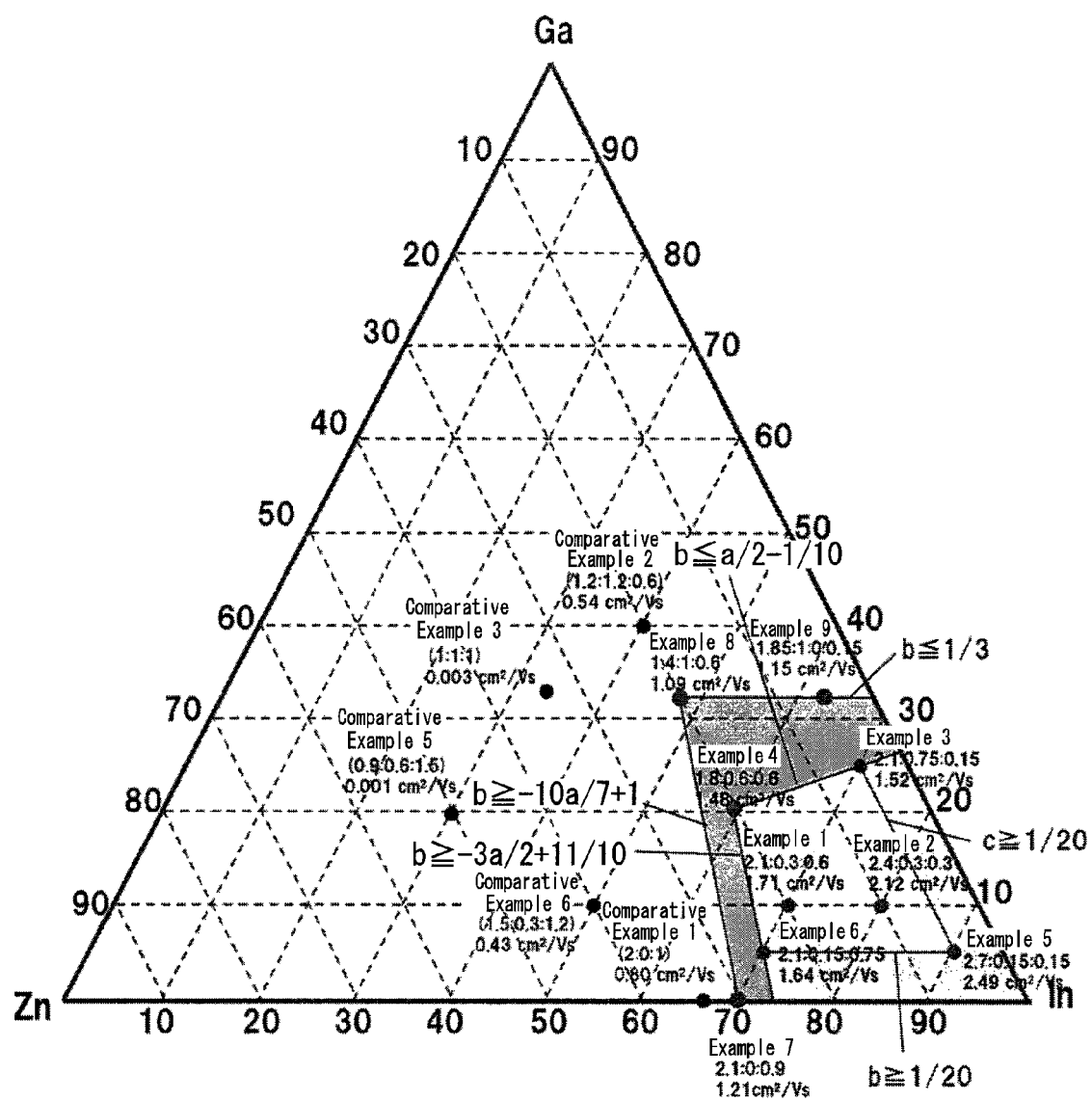
FIG. 9 shows a ternary phase diagram for a composition range in a first region of an oxide semiconductor layer of a thin film transistor according to the invention, and a composition and mobility of a first region of an oxide semiconductor layer of each of Examples and Comparative Examples.

As shown in Table 1 and FIG. 9, it was found that an electron field-effect mobility exceeding 1 cm²/Vs can be achieved when $b \leq 1/3$ and $b \geq -10a/7+1$ are satisfied.

Furthermore, it was found that a higher electron field-effect mobility (1.4 cm²/Vs or more) can be achieved in the composition range satisfying $b \leq a/2 - 1/10$ and $b \geq -3a/2 + 11/10$. This is thought to be because an oxygen vacancy, which acts as a supply source of a carrier, tends to be introduced into the oxide semiconductor due to the relative increase of the indium content. The oxide semiconductor system is reported to exhibit percolation conductivity, and therefore it is assumed that mobility tends to be improved by the increase of the carrier concentration in this case. Furthermore, since 5s orbital of indium is involved in carrier conduction, it is assumed that increase of the indium content in the film naturally leads to the increase in overlapping of electron orbitals, which also contributes to the improvement of mobility.

On the other hand, in Comparative Examples 1 and 2, it was found that the electron field-effect mobility is decreased due to the relatively low indium content.

It is noted that, in such a layered system, the favorable composition range of the oxide semiconductor layer formed by a liquid phase method as in the invention differs from that of the oxide semiconductor layer formed by a vapor deposition method. This is assumed to be because the film formed by the liquid phase method has more trap levels than the film formed by the vapor deposition method as a consequence of contamination by residual organic substances and decrease in film density. Therefore, in the film formation by the liquid phase method, by controlling the composition of the first oxide semiconductor film (the first region), which involved in the carrier conduction, to be more In-rich than that of the film formed by the vapor deposition method, the carrier concentration that contributes to conduction can be increased and high mobility can be realized.

The content of Ga is preferably 5% or more, and the content of In is preferably 5% or more. This is because it is difficult to control carrier in $In_2O_3$ system and InZnO system, and degenerate conduction easily occurs in In-rich region such as a region having a composition according to the invention. Furthermore, the introduction of Ga that suppresses the formation of an oxygen vacancy and is involved in the structural stability can improve the stability over time and stability against repeated driving.

Comparative Examples 3 and 4 are examples in which the oxide semiconductor layer does not have a multi-layered structure but has a single layer structure. As is clear from Comparative Example 3, it was found that, under an identical heat treatment temperature condition, higher mobility can be obtained when the oxide semiconductor layer has a multi-layered structure. As is clear from Comparative Example 4, it was found that higher mobility can be obtained in the TFT having the multi-layered-InGaZnO film annealed at a low temperature compared to the TFT having the single-InGaZnO film annealed at a high temperature.

Composition Dependency in Second Region

The composition of the first region was fixed in a manner similar to Example 1 (a:b:c=2.1:0.3:0.6), and the composition of the second region was changed in the InGaZnO system.

With regard to the TFTs thus produced, the mobility was calculated in a manner similar to the above using a semiconductor parameter analyzer 4156C (manufactured by Agilent Technologies, Inc.). The threshold voltage (Vth) was determined based on I-V characteristics.

The TFT characteristics in the case of changing the composition of the second region is summarized in the following Table 2.

TABLE 2

| | f/(e+f) | Cationic composition of second region | | | Threshold voltage (V) | Electron field-effect mobility (cm²/Vs) |
|---|---|---|---|---|---|---|
| | | e | f | g | | |
| Example 10 | 0.875 | 1/12<br>0.083 | 7/12<br>0.583 | 4/12<br>0.333 | 5.8 | 1.42 |
| Example 11 | 0.750 | 1/6<br>0.167 | 3/6<br>0.500 | 2/6<br>0.333 | 5.1 | 1.71 |
| Example 12 | 0.500 | 1/3<br>0.333 | 1/3<br>0.333 | 1/3<br>0.333 | 4.8 | 1.75 |
| Example 13 | 0.375 | 3/12<br>0.250 | 5/12<br>0.417 | 4/12<br>0.333 | 4.5 | 1.82 |
| Example 14 | 0.250 | 3/6<br>0.500 | 1/6<br>0.167 | 2/6<br>0.333 | −5.2 | 1.85 |

In a case of f/(e+f)=0.875 in which the Ga content is increased (Example 10), it was found that high mobility can be obtained but the mobility is slightly reduced compared to other Examples. This is assumed to be because increase in Ga content in the second region results in increase in resistance in the second region, and therefore resistance between the first region and the source and drain electrodes is increased.

On the other hand, in a case in which the In content is increased as in Example 14 (f/(e+f)=0.250), the threshold value tends to be negatively shifted. It is assumed that, since the carrier concentration in the second region is relatively high in this case, excessive carrier inflow into the first region and partial channel formation in the second region may be occurred. From these results, it was found that a composition range of $0.250 < f/(e+f) < 0.875$ is preferable from the viewpoint of high mobility and $V_{th} > 0$.

Stability Against Repeated Driving

With regard to the TFTs of Examples 1 and 7, a shift amount ($\Delta V_{th}$) of a threshold value from an initial value after applying stress for 300 seconds was measured under stress conditions in which the drain voltage Vd and the gate voltage Vg are fixed at +10 V and +15 V, respectively. The result is shown in Table 3.

TABLE 3

| | Cationic composition of first region | | | Electron field-effect mobility | |
|---|---|---|---|---|---|
| | a | b | c | (cm$^2$/Vs) | $\Delta V_{th}$ |
| Example 1 | 7/10 | 1/10 | 2/10 | 1.71 | +0.8 |
| | 0.700 | 0.100 | 0.200 | | |
| Example 7 | 7/10 | 0 | 3/10 | 1.21 | +1.1 |
| | 0.700 | 0 | 0.300 | | |

It was found that the stability against repeated driving is high in Example 1, since Example 1 in which the first region includes Ga shows a reduced shift amount of a threshold value compared to Example 7 in which the first region includes no Ga.

The thin film transistor produced according to the invention is preferably used as a driving element (driving circuit) in various electronic devices, for example, a device such as a flexible display which can be produced by a low temperature process using a resin substrate; various sensors such as an image sensor such as a CCD (Charge Coupled Device) or a CMOS (Complementary Metal Oxide Semiconductor), and an X-ray sensor; an MEMS (Micro Electro Mechanical System), and the like.

Both the display device and the sensor using the thin film transistor produced according to the invention exhibit favorable characteristics with low power consumption. The "characteristics" referred to herein are the display characteristics in the case of the display device and the sensitivity characteristics in the case of the sensor.

What is claimed is:

1. A method of producing a thin film transistor, comprising:
   forming a gate electrode;
   forming a gate insulating film that contacts the gate electrode;
   forming, by a liquid phase method, an oxide semiconductor layer arranged facing the gate electrode with the gate insulating film provided therebetween, the oxide semiconductor layer comprising a first region and a second region, the first region being represented by $In_{(a)}Ga_{(b)}Zn_{(c)}O_{(d)}$, wherein $a \geq 0$, $b \geq 0$, $c \geq 0$, $a+b+c=1$, $d>0$, $b \leq a/2 - 1/10$, $b \leq -3a/2 + 11/10$, $b \geq 1/20$, and $c \geq 1/20$ are satisfied, the second region being represented by $In_{(e)}Ga_{(f)}Zn_{(g)}O_{(h)}$, wherein $e \geq 0$, $f \geq 0$, $g \geq 0$, $e+f>0$, $h>0$, and $f/(e+f) > 0.250$ are satisfied, and the second region being located farther from the gate electrode than the first region; and
   forming a source electrode and a drain electrode that are arranged apart from each other and are capable of being conductively connected through the oxide semiconductor layer.

2. The method of producing a thin film transistor according to claim 1, wherein, in the forming of the oxide semiconductor layer, a raw material solution comprising a solvent and at least one selected from the group consisting of a metal alkoxide, a β-diketone complex, and a nitrate is used to form the oxide semiconductor layer.

3. The method of producing a thin film transistor according to claim 1, wherein, in the forming of the oxide semiconductor layer, a raw material solution comprising a solvent and at least one selected from the group consisting of a metal alkoxide and a β-diketone complex is used to form the oxide semiconductor layer.

4. The method of producing a thin film transistor according to claim 1, wherein, in the forming of the oxide semiconductor layer, a raw material solution comprising a solvent and a metal alkoxide is used to form the oxide semiconductor layer.

5. The method of producing a thin film transistor according to claim 4, wherein the raw material solution comprises an aminoethanol as the solvent.

6. The method of producing a thin film transistor according to claim 1, wherein, in the forming of the oxide semiconductor layer, a raw material solution comprising a solvent and a β-diketone complex is used to form the oxide semiconductor layer.

7. The method of producing a thin film transistor according to claim 6, wherein the raw material solution comprises a β-diketone as the solvent.

8. The method of producing a thin film transistor according to claim 1, wherein the second region has a composition satisfying $f/(e+f) < 0.875$.

9. The method of producing a thin film transistor according to claim 1, wherein a film thickness of the second region is more than 10 nm but less than 70 nm.

10. The method of producing a thin film transistor according to claim 1, wherein the oxide semiconductor layer is amorphous.

11. The method of producing a thin film transistor according to claim 1, wherein, in the forming of the oxide semiconductor layer, an oxide precursor film including at least one metal organic compound selected from the group consisting of a metal alkoxide and a β-diketone complex is formed, and the oxide precursor film is subjected to a heat treatment at a temperature equal to or higher than a thermal decomposition temperature of the metal organic compound.

12. The method of producing a thin film transistor according claim 11, wherein the heat treatment is carried out at 400° C. or higher.

13. A thin film transistor, produced by the method according to claim 1.

14. A display device, comprising the thin film transistor according to claim 13.

15. An image sensor, comprising the thin film transistor according to claim 13.

16. An X-ray sensor, comprising the thin film transistor according to claim 13.

17. An X-ray digital imaging device, comprising the X-ray sensor according to claim 16.

18. The X-ray digital imaging device according to claim 17, capable of capturing a moving image.

* * * * *